(12) United States Patent
Oishi et al.

(10) Patent No.: US 10,472,250 B2
(45) Date of Patent: Nov. 12, 2019

(54) PIEZOELECTRIC LAYER, PIEZOELECTRIC COMPONENT, PIEZOELECTRIC ACTUATOR, PIEZOELECTRIC SENSOR, HARD-DISK DRIVE AND INK JET PRINTER

(71) Applicant: TDK CORPORATION, Tokyo (JP)

(72) Inventors: Masahiro Oishi, Tokyo (JP); Atsuo Matsutani, Tokyo (JP); Ryu Ohta, Tokyo (JP)

(73) Assignee: TDK CORPORATION, Tokyo (JP)

( * ) Notice: Subject to any disclaimer, the term of this patent is extended or adjusted under 35 U.S.C. 154(b) by 581 days.

(21) Appl. No.: 14/934,988

(22) Filed: Nov. 6, 2015

(65) Prior Publication Data
US 2016/0133825 A1    May 12, 2016

(30) Foreign Application Priority Data
Nov. 12, 2014 (JP) .................................. 2014-229966

(51) Int. Cl.
*H01L 41/18* (2006.01)
*C01G 33/00* (2006.01)
(Continued)

(52) U.S. Cl.
CPC ........ *C01G 33/006* (2013.01); *B41J 2/14233* (2013.01); *H01L 41/0805* (2013.01);
(Continued)

(58) Field of Classification Search
CPC ............... C01G 33/006; B41J 2/14233; H01L 41/0805; H01L 41/0973; H01L 41/1132;
(Continued)

(56) References Cited

U.S. PATENT DOCUMENTS

| 2007/0126313 A1* | 6/2007 | Ueno ................. H03H 9/02031 |
| | | 310/311 |
| 2008/0289426 A1* | 11/2008 | Kearns .................... G01M 5/00 |
| | | 73/632 |

(Continued)

FOREIGN PATENT DOCUMENTS

| JP | 2009-295786 A | 12/2009 |
| JP | 2010-070394 A | 4/2010 |
| JP | 2014-107653 A | 6/2014 |

OTHER PUBLICATIONS

Apr. 1, 2016 Extended Search Report issued in European Patent Application No. 15 19 4334.7.
(Continued)

*Primary Examiner* — Bryan P Gordon
(74) *Attorney, Agent, or Firm* — Oliff PLC

(57) ABSTRACT

A piezoelectric layer made of potassium sodium niobate which is a perovskite type compound represented by the formula $ABO_3$, wherein, in the Raman spectroscopy measurement of the piezoelectric layer which is performed while the piezoelectric layer is rotated in the in-plane direction, the measured intensity of the lattice vibration region of the perovskite type compound in the Raman spectrum obtained in polarized Raman spectroscopy measurement (yx) has a periodicity of approximately 90°, wherein, the polarized Raman spectroscopy measurement (yx) is performed while the piezoelectric layer is rotated in the in-plane direction and Raman scattering light is polarized in a direction perpendicular to that of the incident light.

18 Claims, 9 Drawing Sheets

(51) Int. Cl.
*H01L 41/08* (2006.01)
*H01L 41/113* (2006.01)
*H01L 41/187* (2006.01)
*H01L 41/09* (2006.01)
*B41J 2/14* (2006.01)
*G01N 21/65* (2006.01)
*H01L 41/316* (2013.01)

(52) U.S. Cl.
CPC ...... *H01L 41/0973* (2013.01); *H01L 41/1132* (2013.01); *H01L 41/1873* (2013.01); *B41J 2202/03* (2013.01); *C01P 2002/34* (2013.01); *C01P 2002/82* (2013.01); *C01P 2006/40* (2013.01); *G01N 21/65* (2013.01); *H01L 41/316* (2013.01)

(58) Field of Classification Search
CPC .............. H01L 41/1873; C01P 2002/34; C01P 2002/82; G01N 21/65
USPC ........................................................ 310/358
See application file for complete search history.

(56) References Cited

U.S. PATENT DOCUMENTS

| | | | |
|---|---|---|---|
| 2009/0302715 A1* | 12/2009 | Shibata | H01L 41/1873 310/358 |
| 2010/0066788 A1* | 3/2010 | Hishinuma | B41J 2/14233 347/68 |
| 2011/0074890 A1* | 3/2011 | Miyazawa | H01L 41/0831 347/71 |

OTHER PUBLICATIONS

Wenliang Zhu et al; "Raman tensor analysis of (K0.5Na0.5) NbO3—LiSbO3 lead-free ceramics and its application to study grain/domain orientation", Journal of Raman Spectroscopy, Jul. 11, 2012, pp. 1320-1328, XP055259318.

Rafiq, Muhammad Asif et al., "Precise determination of phonon constants in lead-free monoclinic (K0.5Na0.5)NbO3 single crystals", Applied Physics Letters, 2014, vol. 104, pp. 011902-1-011902-5.

* cited by examiner

PIEZOELECTRIC LAYER, PIEZOELECTRIC COMPONENT, PIEZOELECTRIC ACTUATOR, PIEZOELECTRIC SENSOR, HARD-DISK DRIVE AND INK JET PRINTER

The present invention relates to a piezoelectric layer, a piezoelectric component, a piezoelectric actuator and a piezoelectric sensor using the piezoelectric component, and a hard-disk drive and an ink jet printer using the piezoelectric actuator.

BACKGROUND

In recent years, the demand for lead free in a piezoelectric material is increasing, and thus the study is rising on potassium sodium niobate [(K, Na)NbO$_3$ (hereinafter also referred to as KNN)]. The KNN attracts a lot of attentions because it has a relatively high curie temperature and good piezoelectric properties despite the fact that it is a lead-free piezoelectric material.

With respect to the utilization of the piezoelectric material, the practicality of a film piezoelectric material is developing in place of a bulk piezoelectric material. As an example of the use of such a material, a gyro sensor and a shock sensor or the like where the piezoelectric effect is involved that the force applied to the piezoelectric layer is converted into a voltage, and an actuator, an ink jet head, a loudspeaker, a buzzer, a resonator and the like where the inverse piezoelectric effect is involved that the piezoelectric layer will be deformed when a voltage is applied.

If the piezoelectric material is made as a film, the component may be downsized and can be used in more fields. In addition, as a plurality of components can be prepared in a substrate in a lump, the productivity is increased. Further, there are lots of advantages in terms of performance such as the enhancement of the sensitivity when the piezoelectric material is prepared to be a sensor.

As the indexes for the use of the piezoelectric material, $d_{31}$ or $e_{31}$ which is the piezoelectric constant can be listed. The larger the absolute value is, the better the piezoelectric effect and inverse piezoelectric effect will be.

Among the existing piezoelectric materials, most contain lead such as the representative lead zirconate titanate (PZT). From the viewpoint of environment, a piezoelectric material free of lead is demanded to be developed.

Patent Documents

Patent Document 1: JP-A-2009-295786
Patent Document 2: JP-A-2010-070394

Non-Patent Documents

Non-Patent Document 1: M. A. Rafiq et al., Applied Phisics Letters 104(2014)011902

SUMMARY

However, the piezoelectric layer composed of KNN has a lower piezoelectric constant than the piezoelectric layer using a lead-containing material, so a problem is there that it is hard to provide a big displacement when such a layer is used in a piezoelectric component.

With a low piezoelectric constant, a high voltage is required to provide a big displacement. Further, some technical problems arise such as insulation breakdown or the reliability decreasing in consecutive driving.

In the technique described in Patent Document 1, the piezoelectric constant can be improved by controlling the ratio c/a of the lattice constant c in the out-of-plane direction to the lattice constant a in the in-plane direction within the range of 0.0980 or more to 1.0100 or less in the KNN film. However, in this technique, the lattice constant is controlled by controlling the stress to the film, so the value is likely to be affected by the condition during the film formation or the thickness of the film. Also, the reproducibility is bad.

In the technique disclosed in Patent Document 2, the oxide film with a perovskite structure containing lead as the main component is subjected to a micro-Raman spectroscopy analysis where the Raman spectra with or without an applied electric field are measured. The stress can be reduced if the peak shift in the Raman spectrum is controlled to be 2.2 cm$^{-1}$ or less. However, in the case of the KNN free of lead, even if the peak shift in the Raman spectrum is concerned, no sufficient properties can be provided.

In the technique described in the Non-Patent Document 1, the KNN single crystal of the monoclinic system is subjected to a polarized Raman spectroscopy measurement while being rotated. The polarized Raman spectroscopy measurement (yx) and the polarized Raman spectroscopy measurement (yy) have shown a periodicity according to the rotation angle of the sample. However, the KNN film obtained as a thin film is usually polycrystalline, and it is quite difficult to prepare a KNN film close to a single crystal one. Also, when a single crystal is used in the preparation of a component, the productivity will be low as it will be hard to prepare a plurality of components in a lump.

The present invention is completed in view of the technical problems in the prior art and aims to provide a piezoelectric layer with a further improved piezoelectric constant.

As a big displacement means a high piezoelectric constant, a component utilizing the piezoelectric effect can be applied to a sensor with a high sensitivity or the like, and a component utilizing the inverse piezoelectric effect can be used in an efficient actuator where a big vibration can be provided by a low voltage.

In order to achieve the objective mentioned above, the piezoelectric layer of the present invention is characterized as follows. With respect to the piezoelectric layer composed of potassium sodium niobate which is a perovskite type compound represented by formula ABO$_3$, in the Raman spectroscopy measurement performed while the piezoelectric layer is rotated in the in-plane direction, the measured intensity of the lattice vibration region of the perovskite type compound in the Raman spectrum obtained in the polarized Raman spectroscopy measurement (yx) has a periodicity of approximately 90°, wherein, the polarized Raman spectroscopy measurement (yx) is performed while the sample is rotated in the in-plane direction and the Raman-scattering light is polarized in a direction perpendicular to that of the incident light.

The measured intensity of the lattice vibration region of the piezoelectric layer shows a periodicity of approximately 90° in the Raman spectroscopy measurement, meaning that the lattices match in the plane direction. In this way, the piezoelectric constant increases in the piezoelectric layer, and especially the displacement in the in-plane direction becomes larger.

As the direction of the applied electric field is not parallel to the polarization direction, the stretching behavior in the plane direction when voltage is applied in the thickness direction of the piezoelectric layer will not only contribute to the lattice strain due to the piezoelectric effect but also to the activity of the domain wall. By matching the crystalline structure in the piezoelectric layer in the plane direction, the orientation of the domain wall can be arranged. In this way, the displacement can be effectively increased when compared to that of the piezoelectric layer with a crystalline structure asymmetry in the plane direction.

Further, during the Raman spectroscopy measurement of the piezoelectric layer, in the Raman spectra obtained from the polarized Raman spectroscopy measurement (yy) and the polarized Raman spectroscopy measurement (yx) performed while the sample is rotated in the in-plane direction, the intensity measured in the lattice vibration region of the perovskite type compound shows a periodicity of approximately 90° in both the polarized Raman spectroscopy measurement (yy) and the polarized Raman spectroscopy measurement (yx) and the period of the measured intensity in the polarized Raman spectroscopy measurement (yy) deviates from that in the polarized Raman spectroscopy measurement (yx) by approximately 45°, wherein the polarized Raman spectroscopy measurement (yy) is performed when the Raman-scattering light is polarized in a direction parallel to that of the incident light, and the polarized Raman spectroscopy measurement (yx) is performed when the Raman-scattering light is polarized in a direction perpendicular to that of the incident light. In this respect, the periodicity exists for both the polarized Raman spectroscopy measurement (yx) performed when the Raman-scattering light is polarized in a direction perpendicular to that of the incident light and also the polarized Raman spectroscopy measurement (yy) performed when the Raman-scattering light is polarized in a direction parallel to that of the incident light, thereby further improve the lattice matching and piezoelectric properties.

In the Raman spectroscopy measurement, the information on the short-range order of the crystal lattice of several grains can be obtained. Such a measurement is different from the X-ray diffraction measurement where the long-range order of the lattice can be obtained. The polaxis of the piezoelectrics is closely correlated to the piezoelectric properties, and the periodicity in the Raman spectrum closely relates to the piezoelectric properties of the piezoelectric layer.

In the Raman spectrum measured in the polarized Raman spectroscopy measurement (yx) of the piezoelectric layer, the piezoelectric layer of the present invention has (one or more) peaks in vicinity of 550 $cm^{-1}$ and 610 $cm^{-1}$ respectively with the intensity ratio of the measured intensity of the peak in vicinity of 550 $cm^{-1}$ to that in vicinity of 610 $cm^{-1}$ having a periodicity of approximately 90°. And the difference between the maximal value and the minimal value of the intensity ratio can be controlled to be 0.3 or more and 3.0 or less. The peaks in vicinity of 550 $cm^{-1}$ and 610 $cm^{-1}$ correspond to the stretching vibration of the perovskite type compound, and especially the peak in vicinity of 610 $cm^{-1}$ corresponds to the fully symmetric stretching vibration. The intensity ratio of the stretching vibrations is angle-dependent and the lattice matching can be improved by inducing a difference in the intensity ratio. Further, the piezoelectric properties can be further improved by arranging the polaxis. Here, the term "in vicinity of" in "in vicinity of 550 $cm^{-1}$" or the like refers to a range of ±20 $cm^{-1}$.

With the use of the piezoelectric layer of the present invention, the piezoelectric properties of the piezoelectric component can be improved compared to that using the existing KNN film. In addition, the piezoelectric properties can also be improved in the piezoelectric actuator and piezoelectric sensor of the present invention, and a hard-disk drive and an ink jet printer with high performance can be provided.

The piezoelectric actuator of the present invention is provided with the piezoelectric component having the structure mentioned above. In particular, the piezoelectric actuator can be a head assembly in a hard-disk drive, a piezoelectric actuator in an ink jet printer and the like.

Further, the piezoelectric sensor of the present invention is provided with the piezoelectric component having the structure mentioned above. In particular, the piezoelectric sensor can be a gyro sensor, a pressure sensor, a pulse sensor and the like.

DETAILED DESCRIPTION OF EMBODIMENTS

Figure 1:
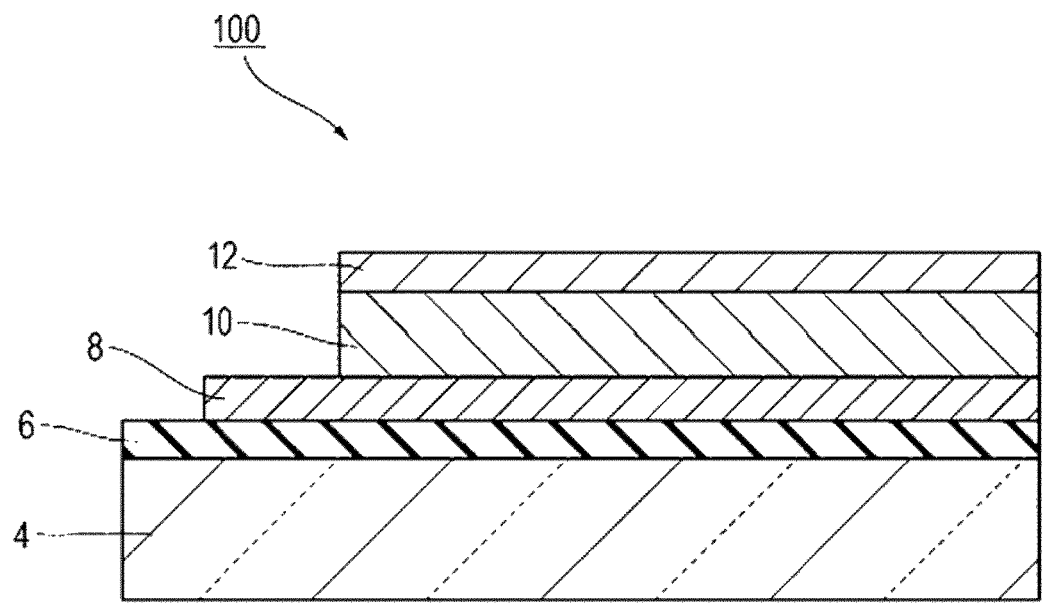
FIG. 1 is a view showing the configuration of the piezoelectric component in the present embodiment.

Hereinafter, a preferable embodiment of the present invention will be described in detail with reference to the drawings. The same or equivalent elements in the drawings are marked with the same symbol. In addition, the positional relationship is shown in the drawings. Further, repeated descriptions will be omitted.

(Piezoelectric Component)

FIG. 1 shows the piezoelectric component 100 in the present embodiment. The piezoelectric component 100 is provided with a substrate 4, an insulting layer 6 and a lower electrode 8 deposited on the substrate 4, a piezoelectric layer 10 formed on the lower electrode 8, and an upper electrode 12 formed on the piezoelectric layer 10.

A silicon substrate with (100) plane orientation can be used as the substrate 4. As an example, the substrate 4 has a thickness of 50 μm or more and 1000 μm or less. Then, the substrate 4 can also be a silicon substrate with a plane orientation other than (100) plane orientation, a substrate of silicon on insulator (SOI), a substrate of silica glass, a semi-conductive substrate composed of GaAs, a substrate of sapphire, a metallic substrate composed of stainless steel or the like, a MgO substrate, a $SrTiO_3$ substrate, and the like.

The insulating layer 6 is used when the substrate 4 is conductive. A film of thermally oxidized silicon ($SiO_2$), $Si_3N_4$, $ZrO_2$, $Y_2O_3$, ZnO, $Al_2O_3$ can be used in the insulating layer 6. When the substrate 4 is not conductive, the insulating layer 6 can be omitted. The insulating layer 6 can be formed through sputtering, vacuum evaporation, thermal oxidation, printing, spin coating method, sol-gel method and the like.

An an example, the lower electrode 8 is made of Pt (platinum). As an example, the lower electrode 8 has a thickness of 0.02 μm or more and 1.0 μm or less. With a lower electrode 8 made of Pt, a piezoelectric layer 10 with good orientation can be formed. The lower electrode 8 can also be made of some metallic materials such as Pd (palladium), Rh (rhodium), Au (gold), Ru (ruthenium), Ir (iridium), Mo (molybdenum), Ti (titanium), Ta (tantalum) and the like; or some conductive oxides of metals such as $SrRuO_3$, $LaNiO_3$ and the like. The lower electrode 8 can be formed through sputtering, vacuum evaporation, printing, spin coating method, sol-gel process and the like.

A (001) plane with fourfold symmetry in plane with respect to the axis in the film formation direction can be found in the lower electrode 8. The lower electrode 8 with fourfold symmetry in plane with respect to the axis in the film formation direction can be formed via vacuum evaporation.

The temperature of the substrate at that time can be controlled at 600° C. or higher and 1000° C. or lower. In this way, a lower electrode 8 with better orientation can be formed.

As the material used in the piezoelectric layer 10, a film of the perovskite type compound of potassium sodium niobate represented by the formula $ABO_3$ can be used. As the additive elements, at least one element selected from the group consisting of Li (lithium), Ti (titanium), Mn (manganese), Sr (strontium), Sb (antimony), Ba (barium), Ta (tantalum), Zr (zirconium) and Bi (bismuth) can be contained. The amount of each element can be controlled at 0.1 at % or more and 5.0 at % or less.

The piezoelectric layer 10 can be formed by a film formation process through sputtering, vacuum evaporation, printing, spin coating method, sol-gel process and the like. The piezoelectric layer 10 is preferred to be a film which specifically has a thickness of 0.5 μm or more and 10 μm or less.

As an example, the upper electrode 12 can be made of Pt. In an example, the upper electrode 12 has a thickness of 0.02 μm or more and 1.0 μm or less. As the upper electrode 12, some metallic materials such as Pd, Rh, Au, Ru, Ir, Mo, Ti and Ta; or some conductive oxides of metals such as $SrRuO_3$ and $LaNiO_3$ can be used. The upper electrode 12 can be formed through sputtering, vacuum evaporation, printing, spin coating method, sol-gel process and the like.

After the film formation is done for the upper electrode 12, an electric field can be applied between the lower electrode 8 and the upper electrode 12 in the piezoelectric component 100. The electric field applied between the lower electrode 8 and the upper electrode 12 can be either a direct current field or an alternating electric field, but is preferred to be a direct current field. In addition, as the method to apply the electric field between electrodes, a manner as follows can be used. That is a direct voltage with an electric field of 1 KV/mm between the electrodes is applied for 1 minute followed by 1 minute of a direct voltage with an electric field of 3 kV/mm between the electrodes and 1 minute of a direct voltage with an electric field of 1 kV/mm. Preferably, the applied electric field changes in several periods.

Figure 6:
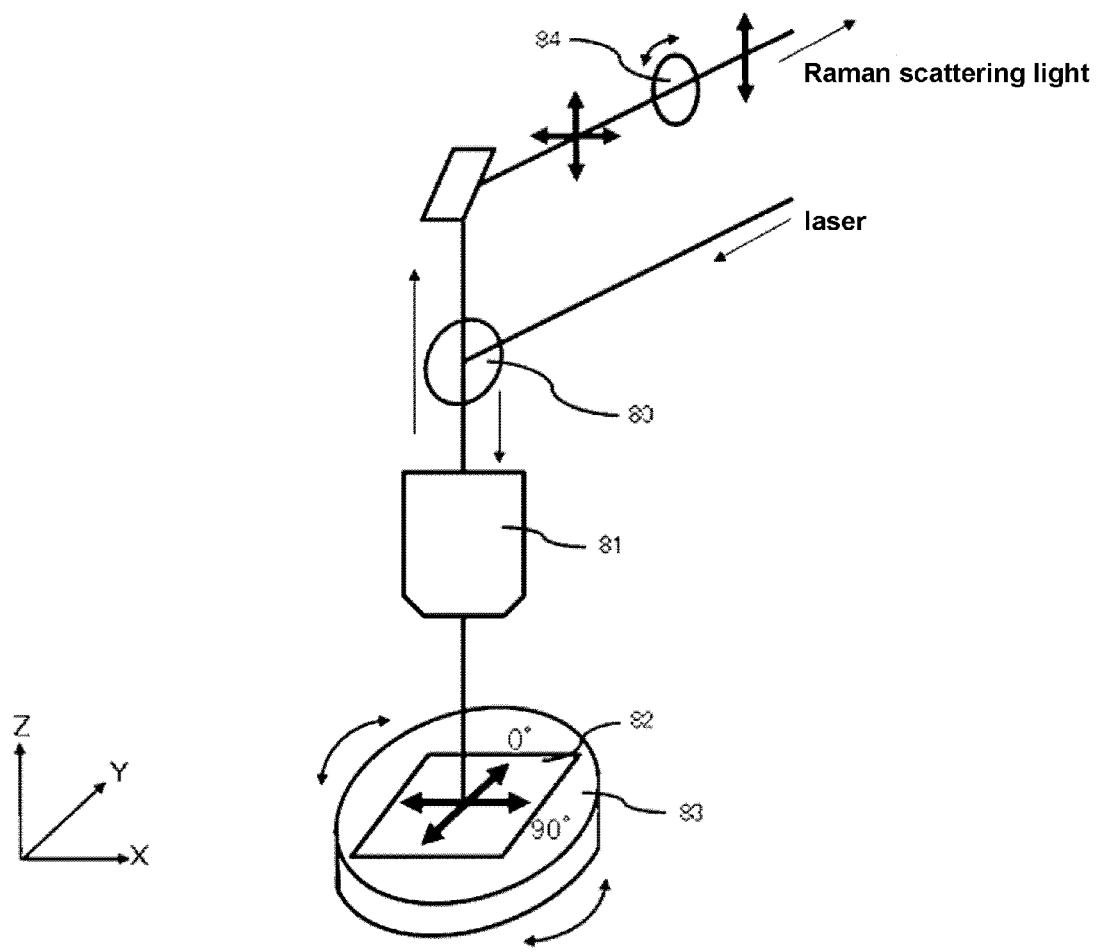
FIG. 6 is a schematic view showing the measuring part in a Raman spectrometer of the present embodiment.

The Raman spectroscopy measurement on the piezoelectric layer 10 is done as follows. After one part of the upper electrode 12 is removed by etching to expose the piezoelectric layer 10, the sample 82 to be measured is set on a rotating stage 83 in the Raman spectrometer as shown in FIG. 6. Then, through the beam splitter 80 and the objective lens 81, the laser is focused on the sample 82. The spectroscopy is performed after the generated Raman scattering light through the object lens 81 and the beam splitter 80 is polarized to 0° or 90° by using the polarizer 84. At that time, the polarized Raman spectroscopy measurement where the Raman scattering light is polarized at 0° is regarded as the polarized Raman spectroscopy measurement (yy) and the polarized Raman spectroscopy measurement where the Raman scattering light is polarized at 90° is regarded as the polarized Raman spectroscopy measurement (yx). The sample is rotated every 5° by the rotating stage 83 in the range of 0° to 180° to perform these polarized Raman spectroscopy measurements, so it is possible to investigate the dependence of the measured intensity of the lattice vibration region on the plane direction in the sample.

In the Raman spectroscopy measurement of the piezoelectric layer 10, the measured intensity in the lattice vibration region has a periodicity of approximately 90°, indicating that lattices match in the plane direction. In this respect, the piezoelectric constant of the piezoelectric layer is increased, and especially the displacement in the in-plane direction becomes larger.

With regard to the piezoelectric layer 10, during the Raman spectroscopy measurement, in the Raman spectrum obtained in the polarized Raman spectroscopy measurement (yx), the measured intensity of the lattice vibration region in the perovskite type compound can have a periodicity of approximately 90°, wherein, the polarized Raman spectroscopy measurement (yx) is performed while the Raman scattering light is polarized in a direction perpendicular to that of the incident light. In this way, the piezoelectric properties can be further improved.

Further, in the Raman spectroscopy measurement of the piezoelectric layer 10, a periodicity of approximately 90° exists in both the polarized Raman spectroscopy measurement (yx) where the spectroscopy measurement is performed while the Raman scattering light is polarized in a direction perpendicular to that of the incident light and also the polarized Raman spectroscopy measurement (yy) where the spectroscopy is performed while the Raman scattering light is polarized in a direction parallel to that of the incident light. In addition, the period of the measured intensity in the polarized Raman spectroscopy measurement (yy) deviates from that in the polarized Raman spectroscopy measurement (yx) by approximately 45°. In this way, the lattice matching can be further improved and the piezoelectric properties can be further improved.

Further, with respect to the Raman spectroscopy measurement on the piezoelectric layer 10, in the Raman spectrum obtained in the polarized Raman spectroscopy measurement (yx) where the spectroscopy is performed while the Raman scattering light is polarized in a direction perpendicular to that of the incident light, there are peaks in vicinity of 550 $cm^{-1}$ and 610 $cm^{-1}$ respectively with the intensity ratio of the measured intensity of the peak in vicinity of 550 $cm^{-1}$ to that in vicinity of 610 $cm^{-1}$ having a periodicity of approximately 90°. By controlling the difference between the maximal value and the minimal value of the intensity ratio at 0.3 or more and 3.0 or less, the lattice matching can be improved and the polaxises can be arranged. In addition, the piezoelectric properties can be further improved.

As an example, the upper electrode 12 can be made of Pt. The upper electrode 12 in an example has a thickness of 0.02 µm or more and 1.0 µm or less. Further, as the upper electrode 12, metallic materials such as Pd, Rh, Au, Ru, Ir, Mo, Ti, Ta and the like, or some conductive oxides of metals such as $SrRuO_3$, $LaNiO_3$ and the like may be used. The upper electrode 12 can be formed through sputtering, vacuum evaporation, printing, spin coating method, sol-gel process and the like.

The substrate 4 can also be removed from the piezoelectric component 100. In this way, the displacement amount or the sensitivity can be increased.

Also, the piezoelectric component 100 can be coated with a protection film so that the reliability can be improved.

In the piezoelectric component 100, an intermediate layer can be deposited between the lower electrode 8 and the piezoelectric layer 10 and/or between the piezoelectric layer 10 and the upper electrode 12.

As the intermediate layer, a conductive oxide can be used. Particularly, $SrRuO_3$, $SrTiO_3$, $LaNiO_3$, $CaRuO_3$, $BaRuO_3$, $(La_xSr_{1-x})CoO_3$, $YBa_2Cu_3O_7$ and $La_4BaCu_5O_{13}$ and the like are preferable because they are highly conductive and highly heat resistant.

(Piezoelectric Actuator)

Figure 2A:
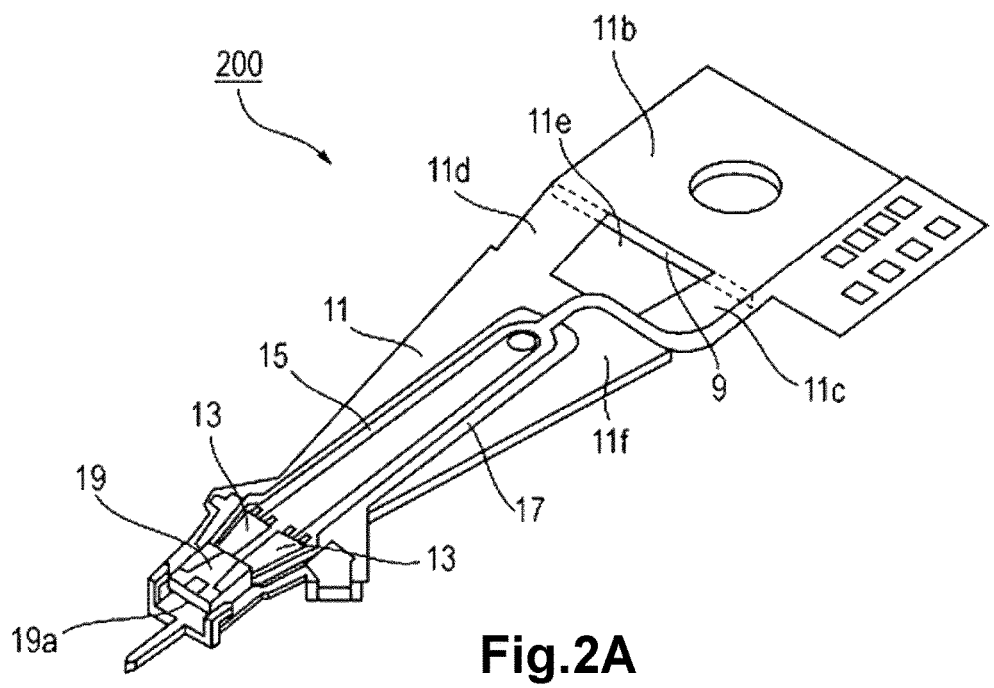
FIG. 2A is a view showing the configuration of the piezoelectric actuator in the present embodiment.

FIG. 2A is a view showing the configuration of a head assembly deposited in a hard-disk drive (hereinafter also referred to as HDD) which is an example of the piezoelectric actuators using the piezoelectric components. As shown in this figure, as the main components, the head assembly 200 is provided with a base plate 9, a load beam 11, a flexure 17, a first and a second piezoelectric components 13 functioning as the actuator components, and a slider 19 with a head component 19a.

The load beam 11 is provided with an end part 11b adhered to the base plate 9 via for example beam welding, a first plate spring part 11c and a second plate spring part 11d elongating from the end part 11b with a shape becoming thinner on the front end, an opening part 11e formed between the first plate spring part 11c and the second plate spring part 11d, and a main part of the beam 11f elongating from the first plate spring part 11c and the second part 11d with a linear shape and becoming thinner on the front end.

The first and the second piezoelectric components 13 are deposited on a flexible substrate for wiring 15 (which is part of the flexure 17) with a specified spacing. The slider 19 is fixed to the front end part of the flexure 17 and rotates as the first and the second piezoelectric components 13 stretch.

The first and the second piezoelectric components 13 each is composed of a lower electrode, an upper electrode and a piezoelectric layer sandwiched between the upper electrode and the lower electrode. By using a piezoelectric layer having a small leakage current and a big displacement amount as the piezoelectric layer used in the piezoelectric actuator of the present invention, good withstand voltage properties and sufficient displacement amount can be provided.

Figure 2B:
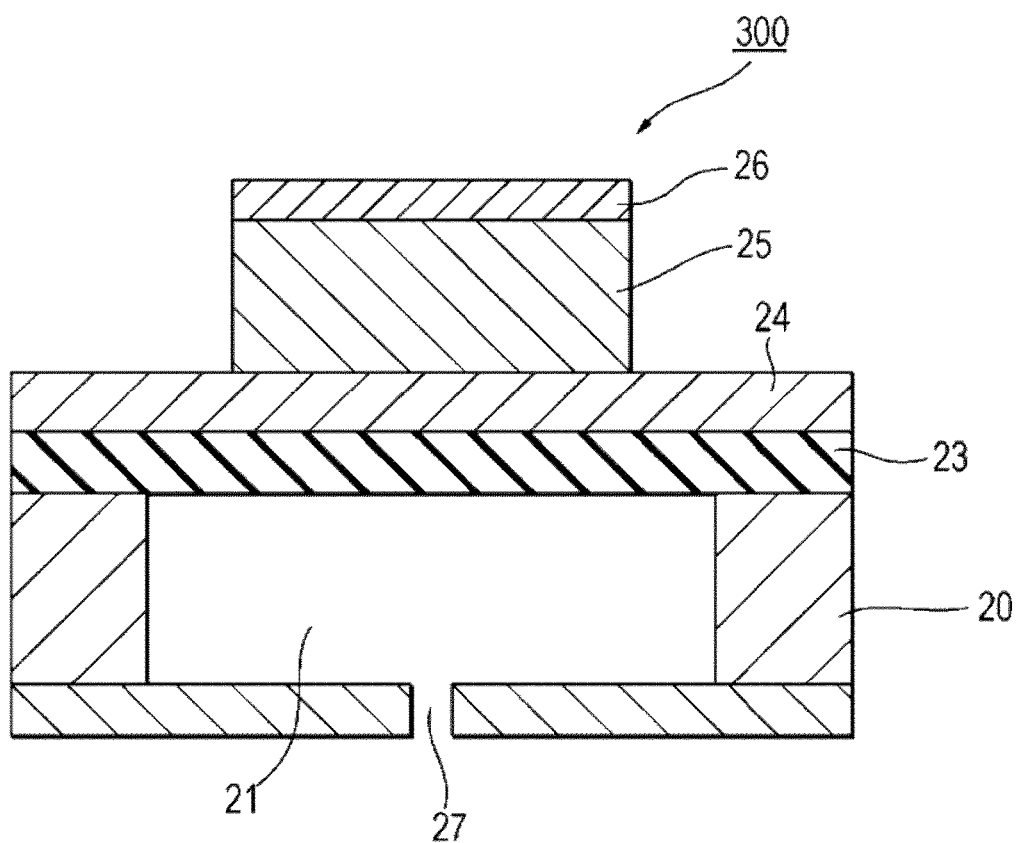
FIG. 2B is a view showing the configuration of a piezoelectric actuator in an ink jet printer head which is another example of the piezoelectric actuator in the present embodiment.

FIG. 2B is a view showing the configuration of a piezoelectric actuator in an ink jet printer head which is another example of the piezoelectric actuator using the piezoelectric component.

The piezoelectric actuator 300 is formed by laminating an insulating film 23, a lower electrode layer 24, a piezoelectric layer 25 and an upper electrode layer 26 on a substrate 20.

When no predetermined spitting out related signal is provided and no voltage is applied between the lower electrode layer 24 and the upper electrode layer 26, the piezoelectric layer 25 will not deform. In a pressure chamber 21 where a piezoelectric component providing no spitting out related signal is deposited, the pressure will not change and no ink will be spit out from the nozzle 27.

On the other hand, when a predetermined spitting out related signal is provided and a definite voltage is applied between the lower electrode layer 24 and the upper electrode layer 26, the piezoelectric layer 25 will deform. In a pressure chamber 21 where a piezoelectric component provided with the spitting out related signal is deposited, the insulating film 23 will bend to a large extent. Thus, the pressure within the pressure chamber 21 will increase in a very short time and ink will be spit out from the nozzle 27.

Here, by using the piezoelectric layer with a small leakage current and a large displacement amount as the piezoelectric layer used in the piezoelectric actuator of the present invention, high withstand voltage properties and sufficient displacement amount can be provided.

(Piezoelectric Sensor)

Figure 3A:
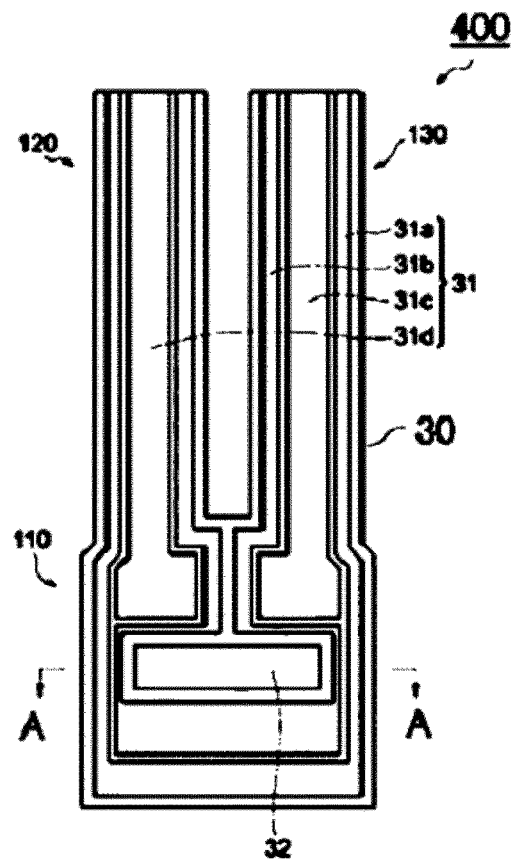
FIG. 3A is a view (planar view) showing the configuration of a gyro sensor which is an example of the piezoelectric sensor in the present embodiment.
Figure 3B:
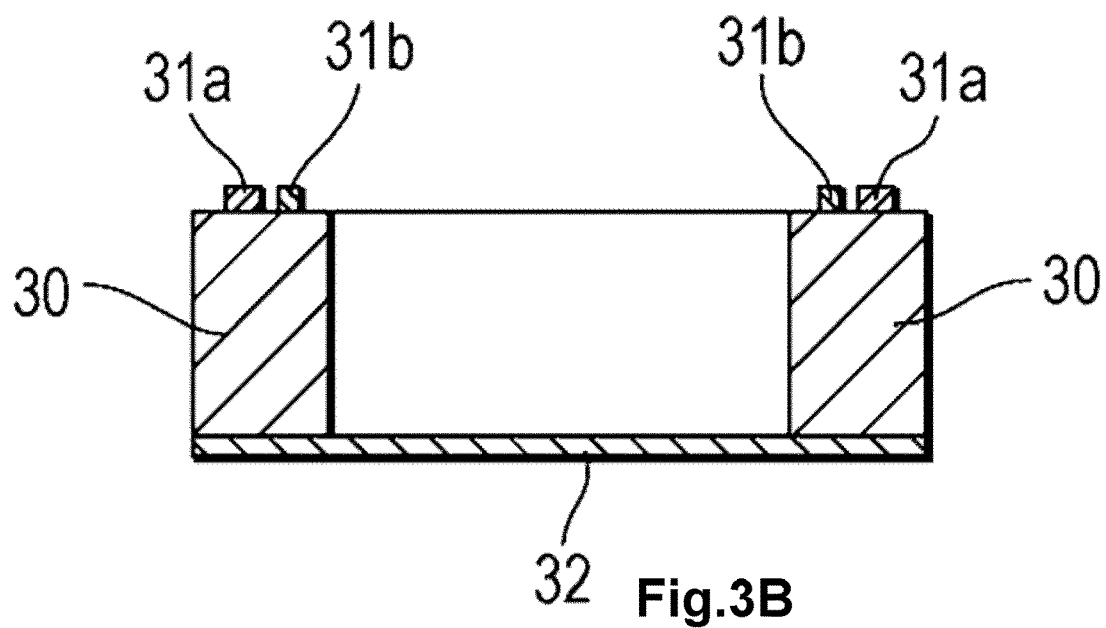
FIG. 3B is a sectional view obtained along the A-A line shown in FIG. 3A.

FIG. 3A is a view (planer view) showing the configuration of a gyro sensor which is an example of the piezoelectric sensor using the piezoelectric component mentioned above, and FIG. 3B is a sectional view obtained from the A-A line of FIG. 3A.

The gyro sensor 400 is a tuning fork oscillator type component for detecting angular velocity and is provided with a base part 110, and two arms 120 and 130 connected to one surface of the base part 110. The gyro sensor 400 is obtained by fine processing a piezoelectric layer 30, an upper electrode layer 31 and a lower electrode layer 32 which constitute the piezoelectric component mentioned above according to the shape of a folk oscillator, and all parts (the base part 110 and the arms 120 and 130) is integrally formed by the piezoelectric component.

Driving electrode layers 31a and 31b and a detecting electrode layer 31d are respectively formed on the first main face of one arm 120. Similarly, driving electrode layers 31a and 31b and a detecting electrode layer 31c are respectively formed on the first main face of the other arm 130. These electrode layers 31*a*, 31*b*, 31*c* and 31*d* are obtained with a specified electrode shape by etching the upper electrode layer 31.

In addition, the solid lower electrode layer 32 formed on the second main face (the main face on the back side of the first main face) of each of the base part 110 and the arms 120 and 130 functions as the ground electrode of the gyro sensor 400.

Here, an XYZ rectangular coordinate system is built up based on that the direction along the long edge of each arm 120 or 130 is regarded as the Z direction, and the plane containing the main faces of two arms 120 and 130 are deemed as the XZ plane.

If a driving signal is provided to the driving electrode layers 31*a* and 31*b*, these two arms 120 and 130 are excited to vibrate in an in-plane vibration mode. The in-plane vibration mode refers to a vibration mode where the two arms 120 and 130 are excited to vibrate in a direction parallel to the main faces of these two arms 120 and 130. For example, one arm 120 is excited to vibrate with a velocity V1 in the −X direction and the other arm 130 is excited to vibrate with a velocity V2 in the +X direction.

If the gyro sensor 400 is supplied with a rotation of an angular velocity ω in that state using the Z axis as the rotating axis, the Coriolis force will respectively affects the two arms 120 and 130 in a direction perpendicular to the velocity direction and these two arms will be excited to vibrate in a out-of-plane vibration mode. The out-of-plane vibration mode refers to a vibration mode where the two arms 120 and 130 are excited to vibrate in a direction perpendicular to the main faces of the two arms 120 and 130. For example, when the Coriolis force F1 affecting one arm 120 is in the −Y direction, the Coriolis force F2 affecting the other arm 130 is in the +Y direction.

The Coriolis force F1 or F2 is proportional to the angular velocity ω. In this respect, the mechanical strain of the arms 120 and 130 caused by the Coriolic force F1 and F2 will be converted into electrical signals (detecting signals) through the piezoelectric layer 30. The signals will be read from the detecting electrode layers 31*c* and 31*d* so as to calculate the angular velocity ω.

By using a piezoelectric layer with a small leakage current and a big displacement amount as the piezoelectric layer used in the piezoelectric sensor of the present invention, good withstand voltage properties and sufficient detecting sensitivity will be provided.

Figure 3C:
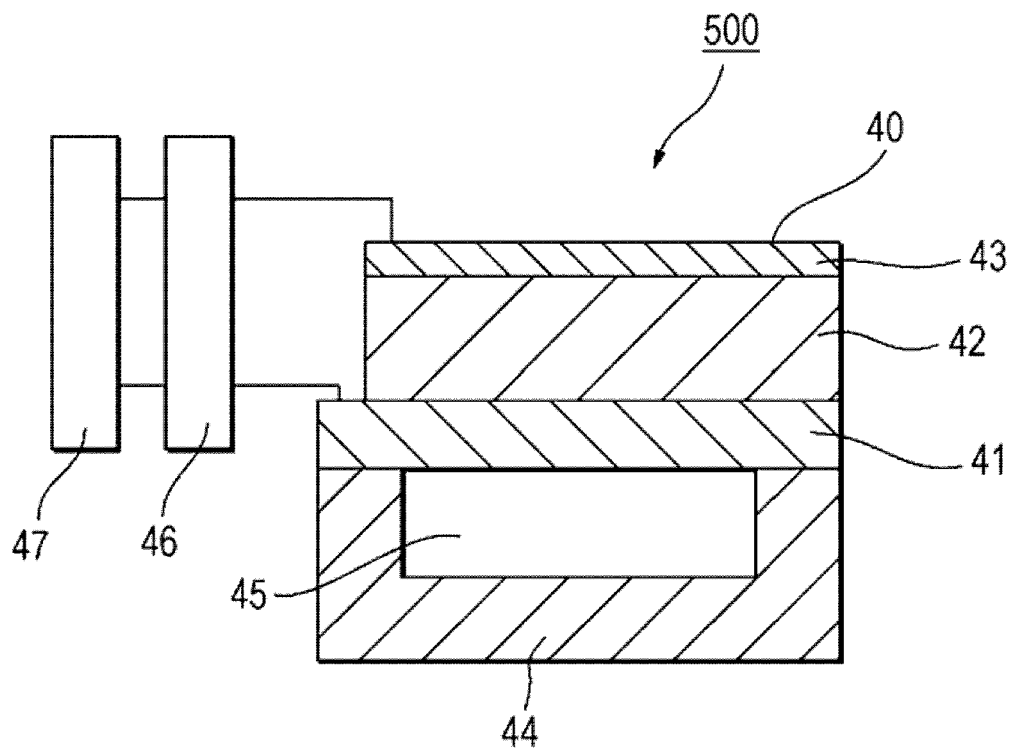
FIG. 3C is a view showing the configuration of a pressure sensor which is the second example of the piezoelectric sensor in the present embodiment.

FIG. 3C is a view showing the configuration of a pressure sensor which is a second example of the piezoelectric sensor using the piezoelectric component mentioned above.

The pressure sensor 500 is provided with a hollow space 45 dealing with the incoming pressure and is composed of a support 44 for supporting the piezoelectric component 40, a current amplifier 46, and a voltage detector 47. The piezoelectric component 40 consists of a common electrode layer 41, a piezoelectric layer 42 and an individual electrode layer 43, and these layers are all stacked on the support 44 in said order. Here, if a force is applied, the piezoelectric component 40 will bend and the voltage can be detected by the voltage detector 47.

By using a piezoelectric layer with a small leakage current and a big displacement amount as the piezoelectric layer used in the piezoelectric sensor of the present invention, good withstand voltage properties and sufficient detecting sensitivity will be provided.

Figure 3D:
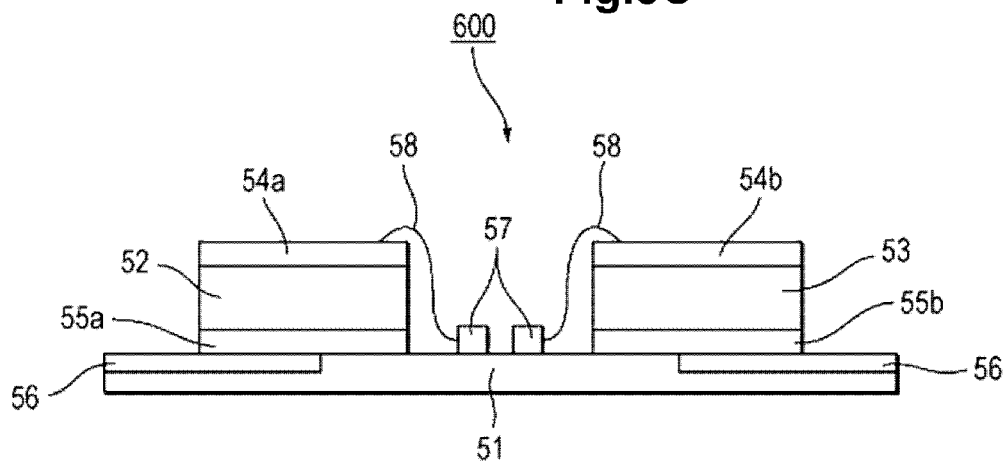
FIG. 3D is a view showing the configuration of a pulse sensor which is the third example of the piezoelectric sensor in the present embodiment.

FIG. 3D is a view showing the configuration of a pulse sensor which is the third example of the piezoelectric sensor using the piezoelectric component mentioned above.

The pulse sensor 600 is provided with a structure where a piezoelectric component for transmitting signals and a piezoelectric component for receiving signals are deposited on the substrate 51. Here, in the piezoelectric component for transmitting signals, electrode layers 54*a* and 55*a* are formed on the two surfaces of the piezoelectric layer 52 for transmitting signals in the thickness direction. In the piezoelectric component for receiving signals, electrode layers 54*b* and 55*b* are formed on the two surfaces of the piezoelectric layer 53 for receiving signals in the thickness direction. In addition, electrodes 56 and electrodes 57 for upper surface are deposited on the substrate 51, and the electrode layers 54*a* and 54*b* are electrically connected to the electrodes 57 for upper surface via the wiring 58, respectively.

During the pulse detection in a living body, the back side of the substrate (where no piezoelectric component is provided) in the pulse sensor 600 is brought to contact the living body. Thereby, specific driving voltage signals are output to the two electrode layers 54*a* and 55*a* in the piezoelectric component for transmitting signals during the pulse detection. In response to the driving voltage signals which are input to the two electrode layers 54*a* and 55*a*, the piezoelectric component for transmitting signals is excited to vibrate and produces ultrasonic waves which are transferred into the living body. The ultrasonic waves transmitted into the living body are reflected by the blood flow, and the signals are received by the piezoelectric component for receiving signals. The piezoelectric component for receiving signals converts the ultrasonic waves into voltage signals which are output from the two electrode layers 54*b* and 55*b*.

By using a piezoelectric layer with a small leakage current as the piezoelectric layer used in the piezoelectric sensor of the present invention, good withstand voltage properties and sufficient detecting sensitivity will be provided.

(Hard-Disk Drive)

Figure 4:
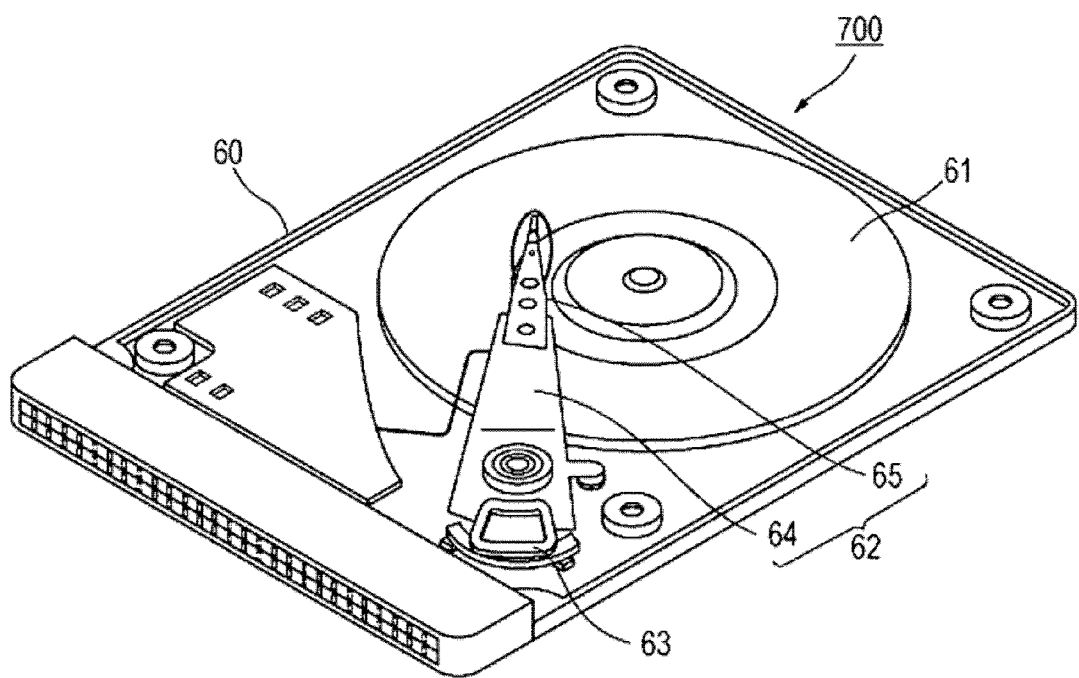
FIG. 4 is a view showing the configuration of a hard-disk drive in the present embodiment.

FIG. 4 is a view showing the configuration of a hard-disk drive provided with the head assembly as shown in FIG. 2A.

Inside the frame 60, the hard-disk drive 700 is provided with a hard disk 61 which functions as a recording medium and a head stack assembly 62 for recording the magnetic information in the hard disk 61 and playing it. The hard disk 61 is forced to rotate by an electric motor not shown in the figure.

The head stack assembly 62 is an assembly formed by stacking several assembling articles in the depth direction of the figure, and the assembling article consists of a actuator arm 64 and a head assembly 65 connected with the actuator arm 64, wherein the actuator arm 64 is supported by the voice coil motor 63 in a manner of that it can rotate freely around the spindle. A slider 19 facing the hard disk 61 is mounted on the front end part of the head assembly 65 (see FIG. 2A).

In the head assembly 65 (200), the head component 19*a* adopt a changing form performed in two steps (FIG. 2A). A relatively large movement of the head component 19*a* is controlled by the driving involving all of the head assembly 65 and the actuator arm 64 induced by the voice coil motor 63 while a minor movement is controlled by the driving of the slider 19 induced by the front end part of the head assembly 65.

In the piezoelectric component used in the head assembly 65, by using a piezoelectric layer with a small leakage current and a big displacement amount as the piezoelectric layer, good withstand voltage properties and sufficient accessibility will be provided.

(Ink Jet Printer)

Figure 5:
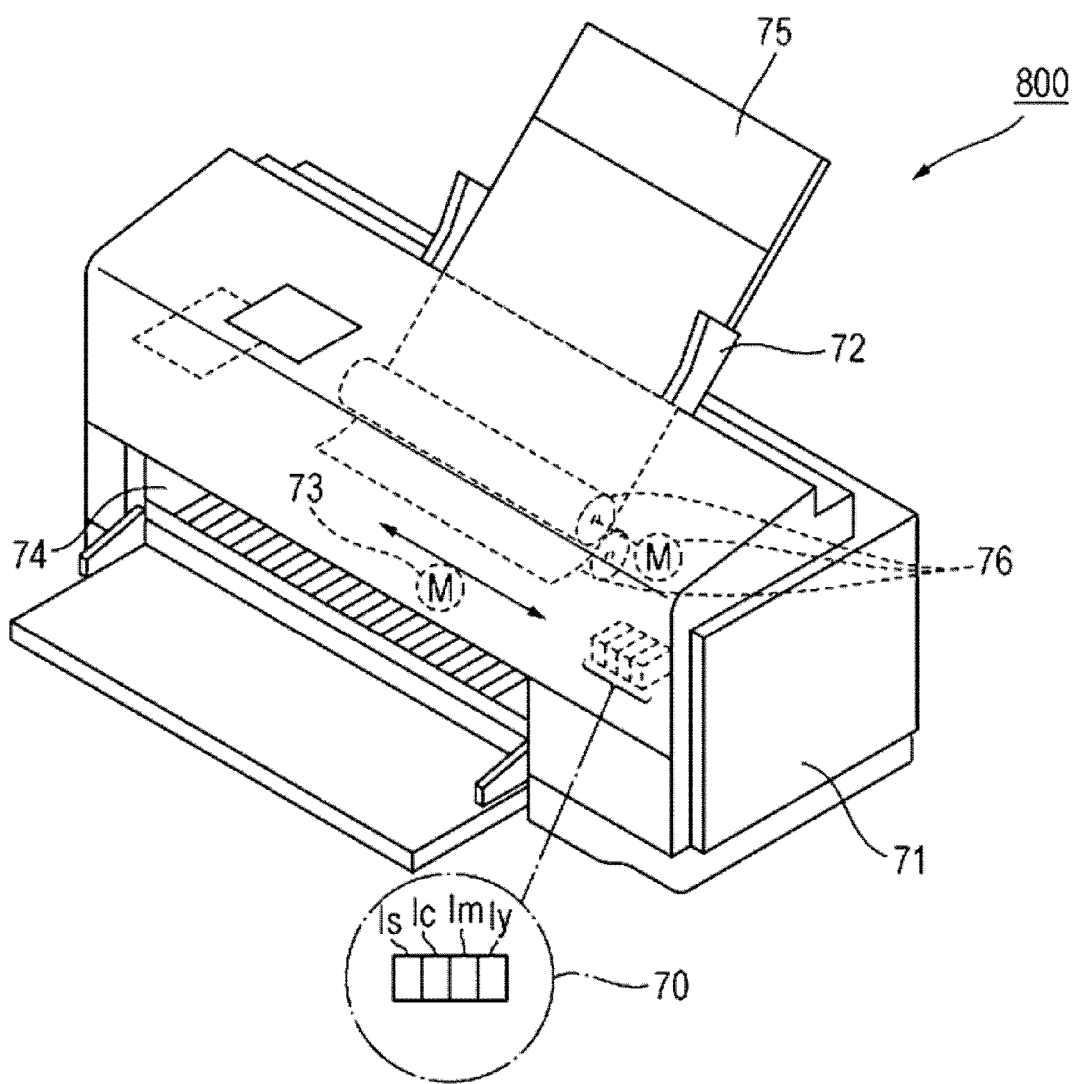
FIG. 5 is a view showing the configuration of an ink jet printer in the present embodiment.

FIG. 5 is a view showing the configuration of an ink jet printer provided with the ink jet printer head as shown in FIG. 2B.

The ink jet printer 800 mainly consists of an ink jet printer head 70, a main body 71, a tray 72 and a head driving device 73. A piezoelectric actuator 300 is deposited inside the ink jet printer head 70.

The ink jet printer 800 is provided with four ink cartridges of four colors, i.e., yellow, magenta, cyan and black, and can provide full-color printing. In addition, the ink jet printer 800 has a dedicated control board and the like in the interior and controls the timing of ink jetting for the ink jet printer head 70 and also the scanning process for the head driving device 73. On the other hand, the main body 71 has a tray 72 on the back and also an automatic sheet feeder 76 (a mechanism for automatically supplying sheets) in the interior. The automatic sheet feeder automatically sends the recording sheet 75 and outputs the recording sheet 75 from the outlet 74 in the front side.

In the piezoelectric component used in the piezoelectric actuator of the ink jet printer head 70, by using a piezoelectric layer with a small leakage current and a big displacement amount as the piezoelectric layer, an ink jet printer with good withstand voltage properties and high security will be provided.

For example, the piezoelectric component having the piezoelectric layer of the present invention can be used in a device where piezoelectric effect is utilized such as a gyro sensor, a shock sensor, a microphone or the like or a device where the inverse piezoelectric effect is utilized such as an actuator, an ink jet head, a loudspeaker, a buzzer, a resonator and the like, preferably a piezoelectric component where the inverse piezoelectric effect is utilized.

EXAMPLES

The present invention will be further described in detail based on Examples and Comparative Examples. However, the present invention is not limited to the following Examples.

(Preparation of a Piezoelectric Component Provided with a Piezoelectric Layer and Raman Spectroscopy Measurement Thereof)

Example 1

In the present Example, a "substrate" refers to an object to be film-formed in each process.

A silicon wafer (substrate 4) with (100) plane orientation and a diameter of 3 inches was put inside a vacuum chamber of a device for vacuum evaporation. After the vacuum-pumping, YSZ (7 mol % $Y_2O_3$—$ZrO_2$) was film-formed as the insulating layer 6 and Pt was film-formed as the lower electrode 8. The substrate temperature during film formation was 900° C. for YSZ (7 mol % $Y_2O_3$—$ZrO_2$) and 700° C. for Pt. The thickness of the insulating layer 6 was 10 nm and the thickness of the lower electrode 8 was 200 nm.

After the lower electrode 8 was film-formed, an out-of-plane XRD (X-Ray Diffraction) was performed to determine the orientation of the direction perpendicular to the surface of the lower electrode 8. The out-of-plane XRD was divided into a symmetric reflection form (i.e., 2θ/θ measurement) where the measurement was performed to the lattice plane that was parallel to the surface of the sample and an asymmetric reflection form where the measurement was performed to the lattice plane that was oblique crossing the surface of the sample. In the present example, the 2θ/θ measurement was performed. According to the results from the 2θ/θ measurement, it was confirmed that Pt oriented towards the (002) plane orientation.

Thereafter, the substrate was moved into a chamber of an RF sputtering device where multiple sputtering targets was mounted. After vacuum-pumping, potassium sodium niobate was film-formed as the piezoelectric layer 10. As the targets for the sputtering, a sintered body of potassium sodium niobate containing 0.25 mol % of Li, 0.25 mol % of Mn and 0.5 mol % of Ta was used. The temperature of the substrate during film formation was 800° C. and the thickness of the piezoelectric layer 10 became 2700 nm.

Then, the substrate was again moved to another chamber of the RF sputtering device. After vacuum-pumping, Pt was film-formed as the upper electrode 12. The temperature of the substrate during film formation was 200° C. and the thickness of the upper electrode 12 became 200 nm.

After the upper electrode 12 was formed, a laminated body containing the piezoelectric layer 10 was patterned by photolithography, dry etching and wet etching. The wafer was cut to provide a piezoelectric component 100 with the mobile part having a size of 5 mm×15 mm.

Thereafter, a direct voltage was applied for 1 minute to provide an electrical field of 1 kV/mm between the lower electrode 8 and the upper electrode 12 in the piezoelectric component 100 followed by a direct voltage for 1 minute to provide an electric field of 3 kV/mm between electrodes and further a direct voltage for 1 minute to provide an electrical field of 1 kV/mm between electrodes.

Then, after one part of the upper electrode 12 in the piezoelectric component 100 was removed by etching to expose the piezoelectric layer 10, a Raman spectroscopy measurement was performed to confirm the short periodicity of the crystal lattice in the piezoelectric layer 10. The Raman spectroscopy measurement was performed twice while the piezoelectric layer was rotated in the in-plane direction, once is the polarized Raman spectroscopy measurement (yy) where the Raman scattering light was polarized in a direction parallel to that of the incident light and the other is the polarized Raman spectroscopy measurement (yx) where the Raman scattering light was polarized in a direction perpendicular to that of the incident light. The spectroscopy measurements were performed with the piezoelectric layer 10 rotated in an angle of 0° to 180° in units of 5°.

Example 2

An MgO substrate (substrate 4) of 15 mm×15 mm×0.5 mm with (100) plane orientation was deposited in a vacuum chamber of an RF sputtering device. Pt was film-formed as the lower electrode 8. The film formation was done with the substrate temperature being 700° C., and the thickness of the lower electrode 8 was made to be 200 nm.

After the lower electrode 8 was film-formed, an out-of-plane XRD (X-Ray Diffraction) was performed to determine the orientation of the direction perpendicular to the surface of the lower electrode 8. The out-of-plane XRD was divided into a symmetric reflection form (i.e., 2θ/θ measurement) where the measurement was done to the lattice plane that was parallel to the surface of the sample and an asymmetric reflection form where the measurement was done to the lattice plane that was oblique crossing the surface of the sample. In the present example, the 2θ/θ measurement was performed. According to the results of the 2θ/θ measurement, it was confirmed that Pt oriented towards the (002) plane orientation.

Thereafter, the substrate was moved into a chamber of the RF sputtering device where multiple of sputtering targets was mounted. After vacuum-pumping, potassium sodium niobate was film-formed as the piezoelectric layer 10. As the targets for the sputtering, a sintered body of potassium sodium niobate containing 0.25 mol % of Li, 0.25 mol % of Mn and 0.5 mol % of Ta was used. The temperature of the substrate during film formation was 750° C. and the thickness of the piezoelectric layer 10 became 2700 nm. The Raman spectroscopy measurement on the piezoelectric layer 10 and the preparation of the piezoelectric component 100 including the treatment with an electrical field were performed as in Example 1.

Example 3

In Example 1, after the orientation of the direction perpendicular to the surface of the lower electrode 8 was determined, the substrate was moved to another chamber in the RF sputtering device. After vacuum-pumping, $SrRuO_3$ was subjected to the film formation to form an intermediate layer. Then, potassium sodium niobate was film-formed as the piezoelectric layer 10. As the targets for the sputtering, a sintered body of potassium sodium niobate containing 0.25 mol % of Li, 0.25 mol % of Mn and 0.5 mol % of Ta was used. The temperature of the substrate during film formation was 700° C. and the thickness of the piezoelectric layer 10 was made to 2700 nm. The Raman spectroscopy measurement on the piezoelectric layer 10 and the preparation of the piezoelectric component 100 including the treatment with an electrical field were performed as in Example 1.

Example 4

In Example 1, after the orientation of the direction perpendicular to the surface of the lower electrode 8 was determined, the substrate was moved to another chamber in the RF sputtering device. After vacuum-pumping, potassium sodium niobate was film-formed as the piezoelectric layer 10. As the targets for the sputtering, a sintered body of potassium sodium niobate containing 0.25 mol % of Li, 0.25 mol % of Mn and 0.5 mol % of Ta was used. The substrate temperature during film formation was 620° C. and the thickness of the piezoelectric layer 10 was made to 2700 nm. Thereafter, the substrate was again moved to another chamber of the RF sputtering device. After vacuum-pumping, Pt was film-formed as the upper electrode 12. The substrate temperature during film formation was 200° C. and the thickness of the upper electrode 12 was made to 200 nm.

After the upper electrode 12 was formed, a laminated body containing the piezoelectric layer 10 was patterned by photolithography, dry etching and wet etching. The wafer was cut to provide a piezoelectric component 100 with the mobile part having a size of 5 mm×15 mm. Then, the Raman spectroscopy measurement was done to the piezoelectric layer 10 as in Example 1.

Example 5

A silicon wafer (substrate 4) of a diameter of 3 inches that was attached with a thermally oxidized film ($SiO_2$: the oxide layer 6) was put into a vacuum chamber of a vacuum sputtering device. After vacuum-pumping, Pt was film-formed as the lower electrode 8. The substrate temperature during film formation of Pt was 300° C. and the thickness of the lower electrode 8 was made to 200 nm.

After the lower electrode 8 was formed by film formation, an out-of-plane XRD (X-Ray Diffraction) was performed to determine the orientation of the direction perpendicular to the surface of the lower electrode 8. The out-of-plane XRD was divided into a symmetric reflection form (i.e., 2θ/θ measurement) where the measurement was done to the lattice plane that was parallel to the surface of the sample and an asymmetric reflection form where the measurement was done to the lattice plane that was oblique crossing the surface of the sample. In the present example, the 2θ/θ measurement was performed. According to the results from the 2θ/θ measurement, it was confirmed that Pt preferably oriented towards the (111) crystal plane.

Then, potassium sodium niobate was film-formed as the piezoelectric layer 10. As the targets for the sputtering, a sintered body of potassium sodium niobate containing 0.25 mol % of Li, 0.25 mol % of Mn and 0.5 mol % of Ta was used. The temperature of the substrate during film formation was 700° C. and the thickness of the piezoelectric layer 10 was made to 2700 nm. The Raman spectroscopy measurement on the piezoelectric layer 10 and the preparation of the piezoelectric component 100 including the treatment with an electrical field were performed as in Example 1.

Comparative Example 1

A silicon wafer (substrate 4) of a diameter of 3 inches that was attached with a thermally oxidized film ($SiO_2$: the oxide layer) was put into a vacuum chamber of a vacuum sputtering device. After vacuum-pumping, Pt was film-formed as the lower electrode. The temperature of the substrate during film formation of Pt was 300° C. and the thickness of the lower electrode was made to 200 nm.

After the lower electrode was formed by film formation, an out-of-plane XRD (X-Ray Diffraction) was performed to determine the orientation of the direction perpendicular to the surface of the lower electrode. The out-of-plane XRD was divided into a symmetric reflection form (i.e., 2θ/θ measurement) where the measurement was done to the lattice plane that was parallel to the surface of the sample and an asymmetric reflection form where the measurement was done to the lattice plane that was oblique crossing the surface of the sample. In the present Comparative Example, the 2θ/θ measurement was performed. According to the results from the 2θ/θ measurement, it was confirmed that Pt preferably oriented towards the (111) crystal plane.

Then, potassium sodium niobate was film-formed as the piezoelectric layer. As the targets for the sputtering, a sintered body of potassium sodium niobate containing 0.25 mol % of Li, 0.25 mol % of Mn and 0.5 mol % of Ta was used. The temperature of the substrate during film formation was 700° C. and the thickness of the piezoelectric layer was made to 2700 nm.

Then, the substrate was again moved to another chamber of the RF sputtering device. After vacuum-pumping, Pt was film-formed as the upper electrode 12. The temperature of the substrate during film formation was 200° C. and the thickness of the upper electrode 12 became 200 nm.

After the upper electrode was formed, a laminated body containing the piezoelectric layer was patterned by photolithography, dry etching and wet etching. The wafer was cut to provide a piezoelectric component with the mobile part having a size of 5 mm×15 mm.

Then, after one part of the upper electrode in the piezoelectric component was removed by etching to expose the piezoelectric layer, a Raman spectroscopy measurement was performed to confirm the short periodicity of the lattice in the piezoelectric layer. The Raman spectroscopy measurement was performed twice while the piezoelectric layer was rotated in the in-plane direction, once is the polarized Raman spectroscopy measurement (yy) where the Raman scattering light was polarized in a direction parallel to that of the incident light and the other is the polarized Raman spectroscopy measurement (yx) where the Raman scattering light was polarized in a direction perpendicular to that of the incident light. The spectroscopy measurements were performed with the piezoelectric layer rotated in an angle of 0° to 180° in units of 10°.

Comparative Example 2

A silicon wafer (substrate 4) of a diameter of 3 inches that was attached with a thermally oxidized film ($SiO_2$: the oxide layer) was put into a vacuum chamber of an RF sputtering device. After vacuum-pumping, Pt was film-formed as the lower electrode. The temperature of the substrate during film formation of Pt was 300° C. and the thickness of the lower electrode was made to 200 nm.

After the lower electrode 8 was film-formed, an out-of-plane XRD (X-Ray Diffraction) was performed to determine the orientation of the direction perpendicular to the surface of the lower electrode. The out-of-plane XRD was divided into a symmetric reflection form (i.e., 2θ/θ measurement) where the measurement was done to the lattice plane that was parallel to the surface of the sample and an asymmetric reflection form where the measurement was done to the lattice plane that was oblique crossing the surface of the sample. In the present Comparative Example, the 2θ/θ measurement was performed. According to the results from the 2θ/θ measurement, it was confirmed that Pt preferably oriented towards the (111) crystal plane.

Then, potassium sodium niobate was film-formed as the piezoelectric layer. As the targets for sputtering, a sintered body of potassium sodium niobate containing no additives was used. The temperature of the substrate during film formation was 700° C. and the thickness of the piezoelectric layer was made to 2700 nm. The confirmation on the orientation of the piezoelectric layer and the preparation of the piezoelectric component were done as in Comparative Example 1.

Figure 7:
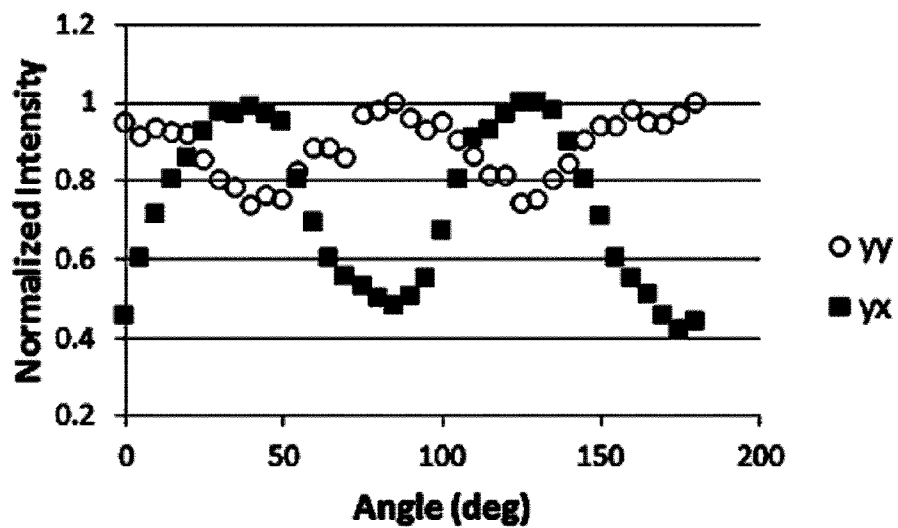
FIG. 7 is a diagram plotting the normalized peak intensity at 220 $cm^{-1}$ corresponding to the $F_{2g}$ deformation vibration of KNN in the polarized Raman spectroscopy measurement (yy) and the polarized Raman spectroscopy measurement (yx) versus each angle to measure, wherein the Raman spectroscopy measurement is performed while the sample of Example 1 is rotated in the in-plane direction.
Figure 8:
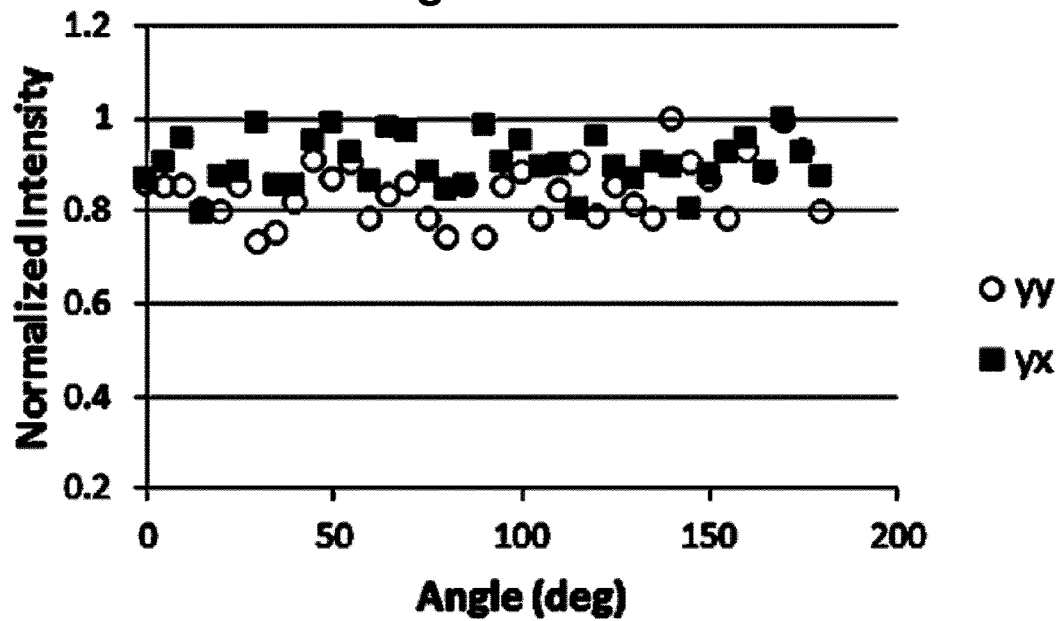
FIG. 8 is a diagram plotting the normalized peak intensity at 220 $cm^{-1}$ corresponding to the $F_{2g}$ deformation vibration of KNN in the polarized Raman spectroscopy measurement (yy) and the polarized Raman spectroscopy measurement (yx) versus each angle to measure, wherein the Raman spectroscopy measurement is performed while the sample of Comparative Example 1 is rotated in the in-plane direction.

The diagrams plotting the normalized peak intensity at 220 cm$^{-1}$ corresponding to the $F_{2g}$ deformation vibration of KNN in the polarized Raman spectroscopy measurement (yy) and polarized Raman spectroscopy measurement (yx) versus each angle to measure in Example 1 and Comparative Example 1 were provided in FIG. 7 and FIG. 8.

Diagrams were also plotted for Examples 2 to 5 and Comparative Example 2. According to each diagram, the angle corresponding to the first maximal value, the angle corresponding to the first minimal value, the angle corresponding to the second maximal value and (the angle corresponding to the second maximal value–the angle corresponding to the first maximal value) in the polarized Raman spectroscopy measurement (yx), the angle corresponding to the maximal value in the polarized Raman spectroscopy measurement (yy) and [the angle corresponding to the maximal value in the polarized Raman spectroscopy measurement (yy)–the angle corresponding to the maximal value in the polarized Raman spectroscopy measurement (yx)] were found. These angles were listed in Table 1.

TABLE 1

| | Angle corresponding to first maximal value in polarized Raman spectroscopy measurement (yx) | Angle corresponding to first minimal value in polarized Raman spectroscopy measurement (yx) | Angle corresponding to second maximal value in polarized Raman spectroscopy measurement (yx) | (Angle corresponding to second maximal value—angle corresponding to first maximal value) in polarized Raman spectroscopy measurement (yx) | Angle corresponding to maximal value in polarized Raman spectroscopy measurement (yy) | [Angle corresponding to maximal value in polarized Raman spectroscopy measurement (yy)—angle corresponding to maximal value in polarized Raman spectroscopy measurement (yx)] |
|---|---|---|---|---|---|---|
| Example 1 | 40° | 85° | 130° | 90° | 85° | 45° |
| Example 2 | 35° | 85° | 125° | 90° | 80° | 45° |
| Example 3 | 0° | 40° | 90° | 90° | 50° | 50° |
| Example 4 | 40° | 80° | 135° | 95° | 85° | 45° |
| Example 5 | 25° | 65° | 110° | 85° | no maximal value | — |
| Comparative Example 1 | no maximal value | no minimal value | no maximal value | — | no maximal value | — |
| Comparative Example 2 | no maximal value | no minimal value | no maximal value | — | no maximal value | — |

As shown in Table 1, (the angle corresponding to the second maximal value–the angle corresponding to the first maximal value) in polarized Raman spectroscopy measurement (yx) was 90°±5° and a periodicity of approximately 90° was found in Examples 1 to 5. However, in Comparative Examples 1 to 2, as there was no maximal value or minimal value, non periodicity was found.

In addition, it can be seen from Table 1 that in Examples 1 to 4, [the angle corresponding to the maximal value in the polarized Raman spectroscopy measurement (yy)–the angle corresponding to the maximal value in the polarized Raman spectroscopy measurement (yx)] was 45°±5°, and the period in the polarized Raman spectroscopy measurement (yx) deviates from that in the polarized Raman spectroscopy measurement (yy) by approximately 45°. However, in Example 5 and Comparative Examples 1 to 2, no periodicity was found as there was no maximal value or minimal value.

Figure 9:
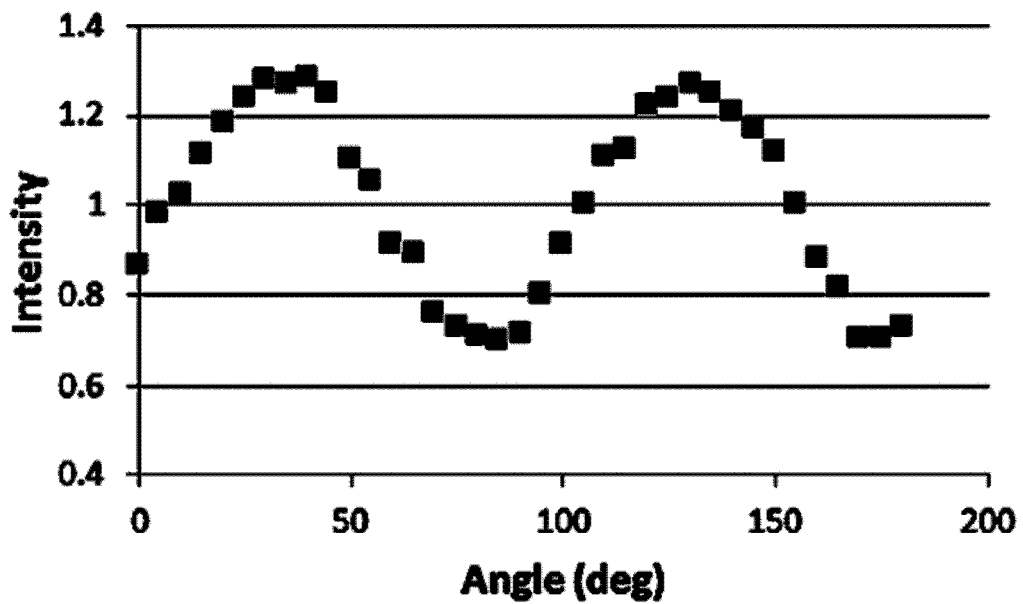
FIG. 9 is a diagram plotting the ratio of the measured intensity of the peak in vicinity of 550 $cm^{-1}$ to that of the peak in vicinity of 610 $cm^{-1}$ in the polarized Raman spectroscopy measurement (yx) versus each angle to measure, wherein the Raman spectroscopy measurement is performed while the sample of Example 1 is rotated in the in-plane direction.
Figure 10:
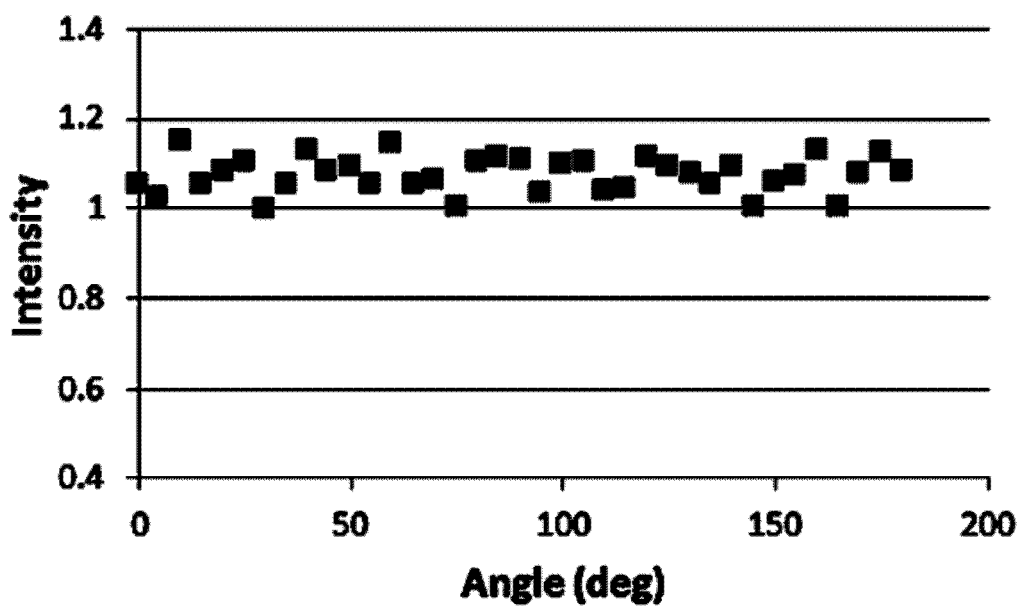
FIG. 10 is a diagram plotting the ratio of the measured intensity of the peak in vicinity of 550 $cm^{-1}$ to that of the peak in vicinity of 610 $cm^{-1}$ in the polarized Raman spectroscopy measurement (yx) versus each angle to measure, wherein the Raman spectroscopy measurement is performed while the sample of Comparative Example 1 is rotated in the in-plane direction.

The diagrams plotting the ratio of the measured intensity of the peak in vicinity of 550 cm$^{-1}$ to that of the peak in vicinity of 610 cm$^{-1}$ in the polarized Raman spectroscopy measurement (yx) versus each angle to measure in Example 1 and Comparative Example 1 were provided as FIG. 9 and FIG. 10.

Diagrams were also plotted for Examples 2 to 5 and Comparative Example 2. The maximal value, the minimal value, (the maximal value–the minimal value) for the ratio of the measured intensity of the peak in vicinity of 550 cm$^{-1}$ to that of the peak in vicinity of 610 cm$^{-1}$ in the polarized Raman spectroscopy measurement (yx) and the situation whether periodicity present or not were determined according to each diagram and then listed in Table 2

TABLE 2

|  | Maximal value for ratio of measured intensity of peak in vicinity of 550 cm$^{-1}$ to that of peak in vicinity of 610 cm$^{-1}$ in polarized Raman spectroscopy measurement (yx) | Minimal value for ratio of measured intensity of peak in vicinity of 550 cm$^{-1}$ to that of peak in vicinity of 610 cm$^{-1}$ in polarized Raman spectroscopy measurement (yx) | Maximal value − minimal value | Periodicity |
|---|---|---|---|---|
| Example 1 | 1.28 | 0.70 | 0.58 | Present |
| Example 2 | 1.29 | 0.76 | 0.53 | Present |
| Example 3 | 1.14 | 0.80 | 0.34 | Present |
| Example 4 | 1.21 | 0.79 | 0.42 | Present |
| Example 5 | 1.25 | 0.98 | 0.27 | Present |
| Comparative Example 1 | 1.15 | 1.00 | 0.15 | Absent |
| Comparative Example 2 | 1.62 | 1.43 | 0.19 | Absent |

As shown in Table 2, in Examples 1 to 5, a periodicity of 90° was found for the ratio of the measured intensity of the peak in vicinity of 550 cm$^{-1}$ to that of the peak in vicinity of 610 cm$^{-1}$ in the polarized Raman spectroscopy measurement (yx). In Comparative Examples 1 to 2, non periodicity was found.

In addition, as shown in Table 2, in Examples 1 to 4, [the maximal value−the minimal value of the ratio of the measured intensity of the peak in vicinity of 550 cm$^{-1}$ to that of the peak in vicinity of 610 cm$^{-1}$ in the polarized Raman spectroscopy measurement (yx)] was 0.3 or more and 1.0 or less. However, in Example 5 and Comparative Examples 1 to 2, the value was smaller than 0.3.

(Assessment on Piezoelectric Component)

The piezoelectric constant −d$_{31}$ was measured as follows. A 3Vp-p of 700 Hz was applied between the upper and lower electrodes in the rectangular sample, and the displacement at the front end part of this rectangular sample was measured by a Laser Doppler displacement meter together with an oscilloscope. The voltage used in measurement was selected based on the consideration that no influence would be produced by the leakage current. However, as a bigger displacement was needed in the piezoelectric component, a higher voltage was required. Then, the piezoelectric constant was calculated according to the following formula (1).

$$d_{31} \cong -\frac{h_s^2}{3L^2}\frac{s_{11,p}}{s_{11,s}}\frac{\delta}{V} \qquad \text{Formula (1)}$$

In the formula, h$_s$ represents the thickness of the substrate; S$_{11,p}$ represents the elastic modulus of the KNN film; S$_{11,s}$ represents for the elastic modulus of the substrate; L represents the length of the driving part; and δ represents the amount of displacement; and V represents the applied voltage.

The value of −d$_{31}$ obtained in the measurement was listed in Table 3 together with the composition in each Example and Comparative Example.

TABLE 3

|  | Composition of electrode/substrate | Additive in the target for piezoelectric layer | Intermediate layer | Treatment with electric field | Piezoelectric constant d$_{31}$ |
|---|---|---|---|---|---|
| Example 1 | Pt/YSZ/Si | Ta 0.5 mol %, Li 0.25 mol %, Mn 0.25 mol % | absent | Yes | −89 |
| Example 2 | Pt/MgO | Ta 0.5 mol %, Li 0.25 mol %, Mn 0.25 mol % | absent | Yes | −83 |
| Example 3 | Pt/YSZ/Si | Ta 0.5 mol %, Li 0.25 mol %, Mn 0.25 mol % | SrRuO$_3$ | Yes | −72 |
| Example 4 | Pt/YSZ/Si | Ta 0.5 mol %, Li 0.25 mol %, Mn 0.25 mol % | absent | No | −78 |
| Example 5 | Pt/SiO$_2$/Si | Ta 0.5 mol %, Li 0.25 mol %, Mn 0.25 mol % | absent | Yes | −65 |
| Comparative Example 1 | Pt/SiO$_2$/Si | Ta 0.5 mol %, Li 0.25 mol %, Mn 0.25 mol % | absent | No | −34 |
| Comparative Example 2 | Pt/SiO$_2$/Si | No additive |  | absent | No | −31 |

It was confirmed that the piezoelectric constant −d$_{31}$ was increased in Examples 1 to 5 when compared to that in Comparative Examples 1 to 2.

It can be seen from the comparison between Example 1 and Example 2 that the piezoelectric constant −d$_{31}$ was further increased in the piezoelectric component where the piezoelectric layer was film-formed after YSZ and Pt was film-formed on the silicon wafer when compared to the piezoelectric component where the piezoelectric layer was film-formed after the Pt was film-formed on the MgO substrate.

As shown in the comparison between Example 1 and Example 3, it was confirmed that the piezoelectric component where the piezoelectric layer was formed by film formation without an intermediate layer had a further increased piezoelectric constant −d$_{31}$.

Based on the comparison between Example 1 and Example 4, it can be known that the piezoelectric component where an electric field was applied after it was prepared had a further increased piezoelectric constant −d$_{31}$ than that without any treatment with an electric field.

When Example 1 was compared to Example 5, it can be confirmed that the piezoelectric constant −d$_{31}$ was further increased in the piezoelectric component where the measured intensity in polarized Raman spectroscopy measurement (yy) deviates from that in polarized Raman spectroscopy measurement (yx) by approximately 45° when compared to the piezoelectric component where the period of the measured intensity in polarized Raman spectroscopy measurement (yy) was uncorrelated to that in the polarized Raman spectroscopy measurement (yx).

As shown in the comparison of Examples 1 to 4 with Example 5 and Comparative Examples 1 to 2, it was confirmed that the piezoelectric constant $-d_{31}$ was further increased in the piezoelectric component where [the maximal value–the minimal value of the ratio of the measured intensity of the peak in vicinity of 550 cm$^{-1}$ to that of the peak in vicinity of 610 cm$^{-1}$ in the polarized Raman spectroscopy measurement (yx)] was 0.3 or more when compared to the piezoelectric component where such a value was smaller than 0.3.

According to the piezoelectric component provided with the piezoelectric layer of the present invention, the piezoelectric properties can be improved when compared to that in the piezoelectric component using the existing KNN film. Further, in the piezoelectric actuator and the piezoelectric sensor involved in the present invention, the piezoelectric properties can be improved. Also, a hard-disk drive and an ink jet printer with high performance can be provided.

DESCRIPTION OF REFERENCE NUMERALS

4 Substrate
6 Oxide film
8 Lower electrode
10 Piezoelectric layer
12 Upper electrode
100 Piezoelectric component
200 Head assembly
9 Base plate
11 Load beam
11b End part
11c, 11d Plate spring part
11e Opening part
11f Main part of beam
17 Flexure
13 Piezoelectric component
19a Head component
19 Head slider
15 Flexible substrate
300 Piezoelectric actuator
20 Substrate material
23 Insulating film
24 Lower electrode
25 Piezoelectric layer
26 Upper electrode
21 Pressure chamber
27 Nozzle
400 Gyro sensor
110 Base part
120, 130 Arm
30 Piezoelectric component
31a, 31b Driving electrode layer
31c, 31d Detecting electrode layer
31 Upper electrode
32 Lower electrode
500 Pressure sensor
45 Hollow space
44 Support
46 Current amplifier
47 Current detector
41 Common electrode layer
42 Piezoelectric layer
43 Individual electrode layer
40 Piezoelectric component
600 Pulse sensor
51 Substrate
52 Piezoelectric layer for signal transmitting
54a, 54b, 55a, 55b Electrode layer
53 Piezoelectric layer for signal receiving
56 Electrode
57 Electrode for upper surface
58 Wiring
700 Hard-disk drive
60 Frame
61 Hard-disk
62 Head assembly
63 voice coil motor
64 Actuator arm
65 Head assembly

What is claimed is:

1. A piezoelectric layer composed of potassium sodium niobate which is a perovskite type compound represented by the formula ABO$_3$,
    wherein, in the Raman spectroscopy measurement of the piezoelectric layer which is performed while the piezoelectric layer is rotated in an in-plane direction, a measured intensity of a lattice vibration region of the perovskite type compound in a Raman spectrum obtained in polarized Raman spectroscopy measurement (yx) has a periodicity of approximately 90°,
    the polarized Raman spectroscopy measurement (yx) is performed while the piezoelectric layer is rotated in the in-plane direction and Raman scattering light is polarized in a direction perpendicular to that of the incident light, and
    a crystal lattice in the piezoelectric layer is matched in a plane direction.

2. The piezoelectric layer of claim 1, wherein, in the Raman spectroscopy measurement of the piezoelectric layer, with respect to the measured intensities of the lattice vibration region of the perovskite type compound in the Raman spectra obtained by performing polarized Raman spectroscopy measurement (yy) and polarized Raman spectroscopy measurement (yx) while the piezoelectric layer is rotated in the in-plane direction, a periodicity of approximately 90° exists in both the polarized Raman spectroscopy measurement (yy) and the polarized Raman spectroscopy measurement (yx), and the period of the measured intensity in the polarized Raman spectroscopy measurement (yy) deviates from that in the polarized Raman spectroscopy measurement (yx) by approximately 45°, and
    the polarized Raman spectroscopy measurement (yy) is performed when the Raman-scattering light is polarized in a direction parallel to that of the incident light, and the polarized Raman spectroscopy measurement (yx) is performed when the Raman-scattering light is polarized in a direction perpendicular to that of the incident light.

3. The piezoelectric layer of claim 1, wherein, in the Raman spectrum obtained by performing the polarized Raman spectroscopy measurement (yx) of the piezoelectric layer, there are at least one peak in vicinity of 550 cm$^{-1}$ and in vicinity of 610 cm$^{-1}$ respectively, and the intensity ratio of the measured intensity of the peak in vicinity of 550 cm$^{-1}$ to that in vicinity of 610 cm$^{-1}$ shows a periodicity of approximately 90°, and the difference between the maximal value and the minimal value of the intensity ratio is 0.3 or more and 1.0 or less.

4. A piezoelectric component comprising an upper electrode and a lower electrode on the piezoelectric layer of claim 1.

5. A piezoelectric actuator using the piezoelectric component of claim 4.

6. A piezoelectric sensor using the piezoelectric component of claim 4.

7. A hard-disk drive comprising the piezoelectric actuator of claim 5.

8. An ink jet printer comprising the piezoelectric actuator of claim 5.

9. A piezoelectric component comprising an upper electrode and a lower electrode on the piezoelectric layer of claim 2.

10. A piezoelectric component comprising an upper electrode and a lower electrode on the piezoelectric layer of claim 3.

11. A piezoelectric actuator using the piezoelectric component of claim 9.

12. A piezoelectric actuator using the piezoelectric component of claim 10.

13. A piezoelectric sensor using the piezoelectric component of claim 9.

14. A piezoelectric sensor using the piezoelectric component of claim 10.

15. A hard-disk drive comprising the piezoelectric actuator of claim 11.

16. A hard-disk drive comprising the piezoelectric actuator of claim 12.

17. An ink jet printer comprising the piezoelectric actuator of claim 11.

18. An ink jet printer comprising the piezoelectric actuator of claim 12.

* * * * *